United States Patent [19]

Hoch

[11] Patent Number: 4,625,877
[45] Date of Patent: Dec. 2, 1986

[54] BLOOD COLLECTION NEEDLE DISPOSAL SYSTEM

[75] Inventor: Louis Hoch, Nutley, N.J.

[73] Assignee: Becton, Dickinson and Company, Franklin Lakes, N.J.

[21] Appl. No.: 795,958

[22] Filed: Nov. 7, 1985

[51] Int. Cl.⁴ ............................................ B65D 85/00
[52] U.S. Cl. .................................................... 215/366
[58] Field of Search ...................... 206/366, 370, 63.5; 215/228

[56] References Cited

U.S. PATENT DOCUMENTS

| | | | |
|---|---|---|---|
| 4,375,849 | 3/1983 | Hanifl | 206/366 |
| 4,453,648 | 6/1984 | Harris et al. | 220/324 |
| 4,454,944 | 6/1984 | Shillington et al. | 206/366 |
| 4,466,538 | 8/1984 | Gianni | 206/366 |
| 4,520,926 | 6/1985 | Nelson | 206/366 |

Primary Examiner—Donald F. Norton
Attorney, Agent, or Firm—R. P. Grindle

[57] ABSTRACT

A closure is provided comprised of a thin flexible material for use on a needle disposal container so that a contaminated blood collection needle may be removed from its holder and deposited in the container without the user touching the needle or the needle hub. The device includes an elongated tapered opening to accommodate varying diameters of needle hubs. A feature of the invention includes a plurality of spaced apart elongated slots extending from each side of the opening which enhances the flexibility of the edges of the opening, which, in turn increases the wedging or wrench-grip action for unscrewing a needle from a collection assembly and at the same time allows ready transfer to a disposal container. The cap of the invention is configured to be utilized with a large variety of collection containers of varying sizes and shapes.

8 Claims, 7 Drawing Figures

BLOOD COLLECTION NEEDLE DISPOSAL SYSTEM

BACKGROUND AND STATEMENT OF THE INVENTION

This invention relates, generally, to receptacles or containers with one-way openings for receiving blood collection needles contaminated with the blood of patients. More particularly, this invention relates to a cap which may be used with a variety of such receptacles which accommodate the user of blood collection needles by allowing for a wrenching action for gripping the hub of the needle so that the needle may be unscrewed from the rest of the collection device and subsequently thrust through the opening of the cap to be disposed of in the associated container. With such an arrangement, users of blood collection needles do not come in contact with any of the needle surface, they are not accidentally punctured by the needles and they do not need to, for any reason, touch the needles or their hubs.

In the last several years, medical practitioners and paramedical technicians have become increasingly aware of the danger of contamination to themselves in the handling of blood collection needles, once a blood specimen has been taken from a patient who may be suffering from some contagious disease. Recently, such dangers have been intensified by the publicity engendered by the rapid increase in the spread of the Acquired Immune Deficiency Syndrome (AIDS) Virus. For that one disease alone, it is extremely important that no blood contact be made between the medical technician or practitioner's blood, and the blood of a diseased patient.

A further problem arises later, of course, after the technician or practitioner has disposed successfully of the contaminated needle without being contaminated by the needle. That is, if such needles are simply discarded in the trash of a hospital or clinic, for example, anyone handling the garbage in the long succession of the passage of the garbage from the institution to a garbage dump may be exposed to contamination by those needles simply by someone grasping a bag containing such needles and puncturing their finger, for example. Moreover, such needles may be laid aside by a physician or technician during a difficult procedure, without thinking, and someone might lean against a table or shelf where the contaminated needle is lying and contaminate their own blood with a blood sample from the needle.

While awareness of the contamination problem has increased considerably in the last two or three years, the danger of contamination has been around for a long time and a wide assortment of devices have been provided through the years to make disposal techniques safe and fast. Some devices, for example, have been developed to receive contaminated needles through an opening in the top of a container which cannot be opened. That is, the opening is surrounded by a plurality of integral flaps which are flexible and allow receipt of a sharp object through the opening. However, no one can remove the sharp objects passing through the opening in the opposite direction. This arrangement is satisfactory, providing that the needle does not have to be removed from the rest of the collection device. However, such an arrangement does not allow removal of the contaminated needle from a holder so that the holder itself may be utilized for subsequent blood collections. It follows that manual separation is required which invites contamination. Representative of such devices are containers such as those described and claimed in U.S. Pat. Nos. 4,520,926 and 4,454,944. Both of these patents include arrangements for receiving not only single and multiple sample blood collection needles, but also syringes including the entire body of the syringe.

A further arrangement of blood collection needle receiving containers for contaminated needles is taught in U.S. Pat. No. 4,466,538. The arrangement in that patent not only provides a one-way opening for receiving contaminated needles, but also, the opening includes a tapered configuration. The point of the tapered walls of the opening is to allow a large opening at one end to receive the hub of a needle. Thus, the user may move the needle hub in the opening from the large end of the opening to a more narrow portion of the opening in order to provide a wedging action so that the user may unscrew the needle hub from the rest of the blood collection assembly. Subsequent to the unscrewing manipulation, the released needle and hub are moved back toward the larger portion of the opening so the needle and hub will pass through the opening into the container below.

Difficulties have taken place in the use of such arrangements, however, in that the needle hubs have a tendency to become "hung-up" in the narrow portion of the opening so that the user must manually unwedge and move the needle hub from the narrow portion of the opening to the wider portion so that the needle and hub will drop in. This, of course, creates the danger that the technician may become contaminated with blood on the contaminated needle during this maneuver to attempt to remove the needle hub from its wedged position in the opening.

This patent also includes the provision of the top surface of the cap having a slanted top surface so as to encourage the movement of the needle hub, once it has been unscrewed from the blood collection assembly to move downwardly toward the enlarged portion of the opening in the slanted surface of the cap of the container. Nevertheless, even with the downward slant of the opening, needle hubs become wedged readily in the narrow portion during the unscrewing or wrenching action necessary or required to unscrew the needle hub from the opening.

In U.S. Pat. No. 4,375,849 a collection cup of the kind discussed herein is designed to include a cap having a specially shaped opening for bearing engagement by the cartridge structure of a double ended needle unit to permit unthreading of the needle unit from a syringe barrel as a one-handed operation, whereupon the thus-separated needle unit is intended to fall into the collection cup without direct handling by the technician. However, such cap constructions have not prevented occasional jamming of the needle unit, as discussed above with respect to U.S. Pat. No. 4,466,538 such that it becomes necessary to dislodge the needle unit manually resulting in possible contamination or injury. Other collection cup designs have included a movable cap which can be closed when the cup is full to permit cup handling for disposal purposes without contacting the used needles. However, cap constructions of this type have been susceptible to relatively easy reopening, sometimes inadvertently, resulting in potential contamination, injury, or unauthorized reuse.

With this invention, by contrast, a cap or closure is provided for incorporation into a contaminated blood collection needle assembly with the surface thereof comprised of a thin flexible material which gives upon contact or receipt of a needle assembly through the opening disposed in the cap or closure. The arrangement of the invention here includes a specific configuration of opening having tapered walls in the manner discussed above with respect to the prior art. However, incorporated with the opening are a plurality of elongated slots extending from each side of the opening which provide a flexible wrenching action for the hub of a needle assembly thrust into the opening. That is, the flexible material of the cap "gives" with such a thrusting movement and then grips the hub and provides a wrenching action allowing the technician to unscrew the hub from the rest of the blood collection assembly.

Once this unscrewing action has taken place, the wrenching action is overcome simply by a further thrusting forward of the hub through the opening because of the built-in flexibility of the edges of the opening, in accordance with this invention. The tapered opening of the invention is such, that, alternatively, the unscrewed hub of the needle assembly may simply be moved toward the enlarged end of the opening for it to fall through the opening. At any rate, the flexibility of the engaging surfaces of the opening in combination with the elongated slots placed in strategic locations along each side edge thereof provides the appropriate gripping action for the hub for obtaining the unscrewing action required to release the hub from the rest of the collection assembly while still not causing the hub to be "hung-up" and wedged into the opening as was the case with the previous arrangements with rigid edges for the opening.

As a further feature of the invention herein, the specific combination of opening in the cap of the invention may be placed in a cap surface which is horizontal, or perpendicular to the axis of the cap. However, the top surface of the invention here may be inclined in the same manner as taught in the prior art patents discussed above but in the reverse direction, the incline downwardly being toward the small end of the opening. Such a slanted surface enhances the movement of the holder toward the wedging position for increasing the wrenching action to unscrew the hub from the rest of the assembly.

As purely illustrative of materials which may be used to form the flexible closure of the invention, one may select, for example, polypropylene. Another representative thermoplastic material is acrylonitrile-butadiene-styrene terpolymer. Furthermore, a thin flexible metallic cap may be utilized. The cap or closure of the invention, if it is made of a thermoplastic material, may be stamped, vacuum formed or injection molded. Preferably, the material will be polypropylene formed to have the major surface of the cap of a thickness of 1.27 mm. The range of thickness of the surface of the cap of the invention may be within the range of between about 0.1 and 2.0 mm. The dimension of the opening will be discussed in more detail below in the description of the drawings herein. However, it should be noted that the dimension of the opening is sized to accommodate any of the conventional needles on the market, such as those of Terumo, Sherwood and Becton, Dickinson and Company.

With the foregoing and additional objects in view, this invention will now be described in more detail, and other objects and advantages thereof will become apparent from the following description, the accompanying drawings, and the appended claims.

IN THE DRAWINGS

DETAILED DESCRIPTION OF THE DRAWINGS

Figure 1:
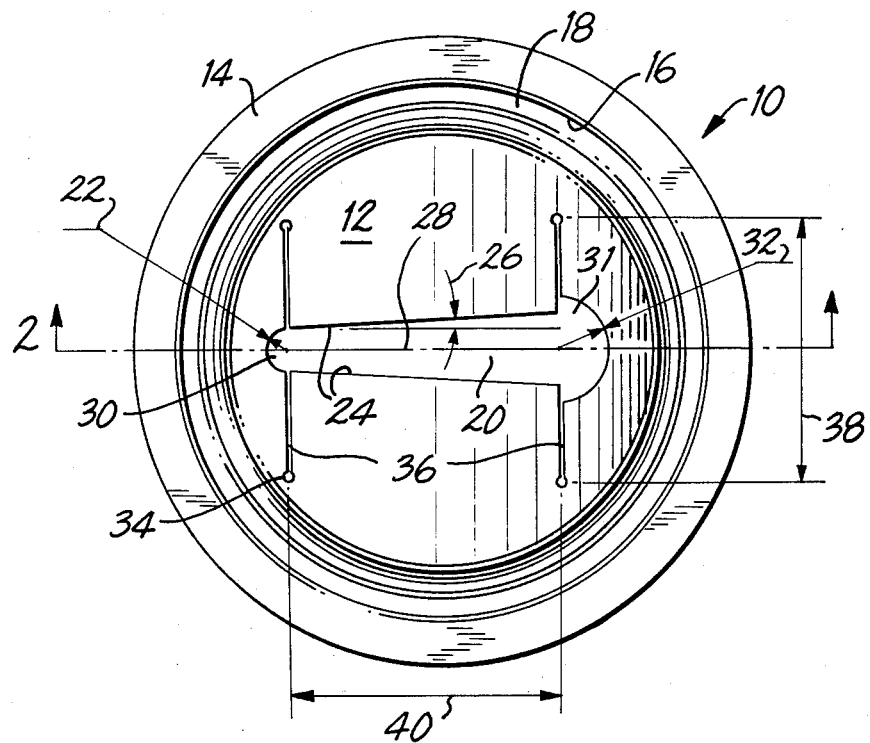
FIG. 1 is a top plan view of a container closure for use in a sharps collection container assembly, and illustrating the configuration of opening of the invention herein.

Referring to the drawings in which like reference characters refer to like parts throughout the several views thereof, an embodiment of apparatus incorporating the invention herein is illustrated in the form of a cap for closing the opening in a blood collection needle disposal system including a container therefore. It will be understood by practitioners-in-the-art, that the cap illustrated in FIG. 1 and the alternative embodiment in FIG. 5 may be utilized and incorporated into a collection container assembly wherein the container may be of a variety of configurations including rectangular, square or round in shape and of a variety of sizes depending upon the specific application of the collection assembly in a particular location in a hospital or clinic, for example. Thus, in FIG. 1, a cap 10 is shown illustrating the invention having an outer flange 14 surrounding the top surface 12 of the cap 10. Disposed between the outer flange 14 and the top surface 12 of cap 10 is an annular vertical wall 16 and a groove 18 to be described in more detail below. As discussed above, top 12 may be comprised of vacuum formed polypropylene, for example, having a thickness of about 1.27 mm. and vacuum formed into the configuration shown. In this connection, it should be understood that cap 10 may be square or rectangular, as well, depending upon the opening upon which it is to be used.

In accordance with the invention herein, an opening 20 is disposed in the top surface 12 of cap 10. As shown, opening 20 has tapered side walls 24 diverging from small end 30 toward large end 31 of opening 20. These diverging walls allow for differing dimensions of the width of opening 20 to accommodate varying sizes of needle hubs on the market. While the material making up the top surface 12 of cap 10 is flexible, as discussed above because of the material utilized and the thickness thereof, it is important to note that in accordance with this invention, opening 20 has disposed adjacent each side thereof spaced apart slots 36 which extend to very small circular openings 34. These slots 36 have the property of enhancing the flexibility of the tapered side edges 24 of opening 20 so as to allow the user of the device to grip the needle holder to be removed from a blood collection device so that the holder may be unscrewed and released from the rest of the collection assembly. This very same flexible property allows for readily thrusting the released holder hub with attached contaminated needle or needles through the opening 20 and into the container itself.

While it will be understood by practitioners-in-the-art that cap 10 will have varying dimensions depending upon the specific container into which it will be incorporated and the use for which the container will be made (i.e., heavy duty use or light duty use in various locations in a clinic or hospital) as purely illustrative of dimensions of the embodiment of cap illustrating the invention herein one may note that the angle 26 of taper of side walls 24 may be about three degrees from the longitudinal axis of opening 20. The radius 22 of end 30 of opening 20 may be, for example, 1.46 mm. while the radius 32 of opening 31 may be 4.66 mm. The dimension 38 may be, for example, 21.74 mm. while the dimension 40 may be, for example, 22.22 mm. The overall diameter of cap 10 may be, in this embodiment, 49.88 mm. although this dimension will vary depending on the opening to be closed, and has little relationship to the dimensions of opening 20. In order to provide the flexibility of surface 12 of cap 10 in accordance with this invention, the slots 36 end in circular openings having a dimension which may be, for example, 1.58 mm. Slots 36 will be, for example, 0.38 mm. wide.

It should be understood, that all of these dimensions are representative only of a specific embodiment of the invention as discussed herein. The dimensions will vary, as will be understood by practitioners-in-the-art depending upon the specific application of the container device, as discussed above.

Figure 2:
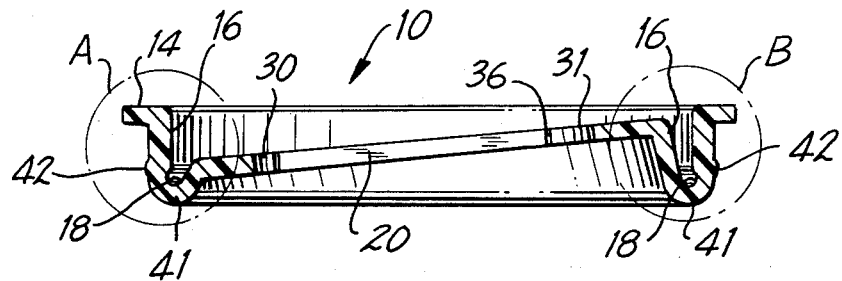
FIG. 2 is a sectional view taken along lines 2—2 of FIG. 1.

Referring now to FIG. 2, a sectional view of cap 10 is shown. As can be seen in FIG. 2, an annular flange 14 extends around the top surface of cap 10. Furthermore, as can be seen in FIG. 2, the top surface 12 of cap 10 is slanted downwardly from the right-hand edge thereof to the left-hand edge thereof. The annular flange 14 is connected to a substantially vertical wall 16 which extends downwardly to a groove 18 which is formed by the connection 41 between the annular wall 16 and the top surface 12 of the cap assembly of the invention. An annular abutment 42 is shown which serves to provide a wedging action for fitting cap 10 upon a collection container for providing a blood collection needle disposal system. It should be understood, however, that cap 10 may be incorporated into and be integral with such a container when it is formed.

Figure 3:
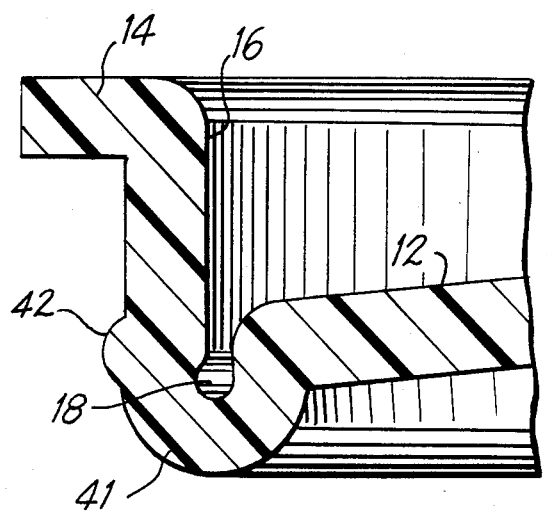
FIG. 3 is an enlarged sectional view of that portion of FIG. 2 shown in the circle "A" of FIG. 2.
Figure 4:
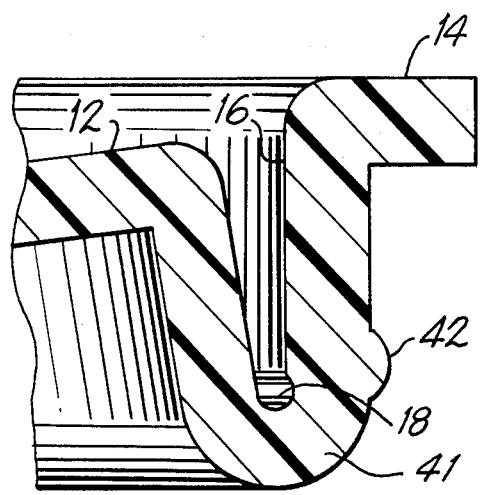
FIG. 4 is an enlarged sectional view of that portion in the circle designated "B" in FIG. 2.

Referring now to FIG. 3, an enlarged sectional view is shown of that portion of FIG. 2 in the circle designated "A" in FIG. 2. The enlargement shows in the sectional view thereof the left-hand end of the cap shown in FIG. 2 and details the configuration of the connection 41 forming the groove 18 and the annular abutment 42. The same comments can be made with respect to FIG. 4 which shows the same details of cap assembly 10.

Figure 5:
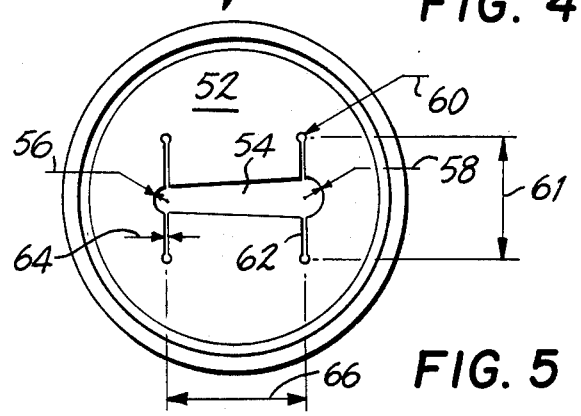
FIG. 5 is a top plan view of a further embodiment of the invention herein showing the major surface of the closure of that embodiment being horizontal, or perpendicular to the axis thereof.
Figure 6:
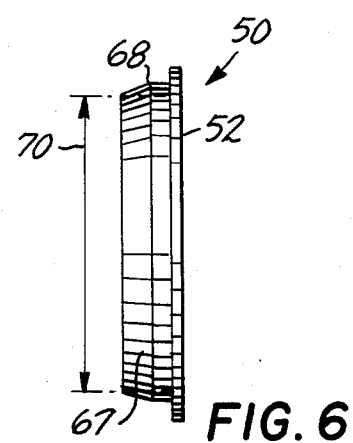
FIG. 6 is a side elevational view of the closure of FIG. 5

Referring now to FIG. 5, a further embodiment of cap assembly 50 is shown. As can be seen in this embodiment, an opening 54 is positioned in the top surface 52 of cap 50. The opening 54 is arranged and configured in the same manner as opening 20 in the embodiment shown in FIG. 1. As can be seen in FIG. 6, however, the top surface 52 is flat in this assembly, with no incline. Thus, the cap 50 shown in this assembly includes a depending skirt 67 with an annular wedge 68 for press fitting cap 50 into an opening of a blood collection needle disposal container for receiving needles thrust through opening 54 of cap 50. As purely illustrative of dimensions of the embodiment of cap 50 shown in FIGS. 5 and 6, dimension 66 is 22.22 mm. while dimension 61 is 19 mm. and the thickness 64 of slots 62 is 0.794 mm. The diameter of small end 56 of opening 54 is 3.45 mm. while the diameter of large end 58 of opening 54 is 6.13 mm. The dimension 70 is 49.91 mm. Again, it should be emphasized here that these dimensions are representative only to illustrate the relationship of dimensions among the various parts of the cap or closure of the invention in order to provide the proper working action of the cap. Simultaneously the gripping and wrenching action necessary for unscrewing a needle hub is provided while at the same time there is sufficient flexibility to allow the released hub to become unwedged so as to be discarded through the opening without any unnecessary catching or wedging action requiring a manual manipulation to remove the released hub from the opening to allow it to fall into the container.

Figure 7:
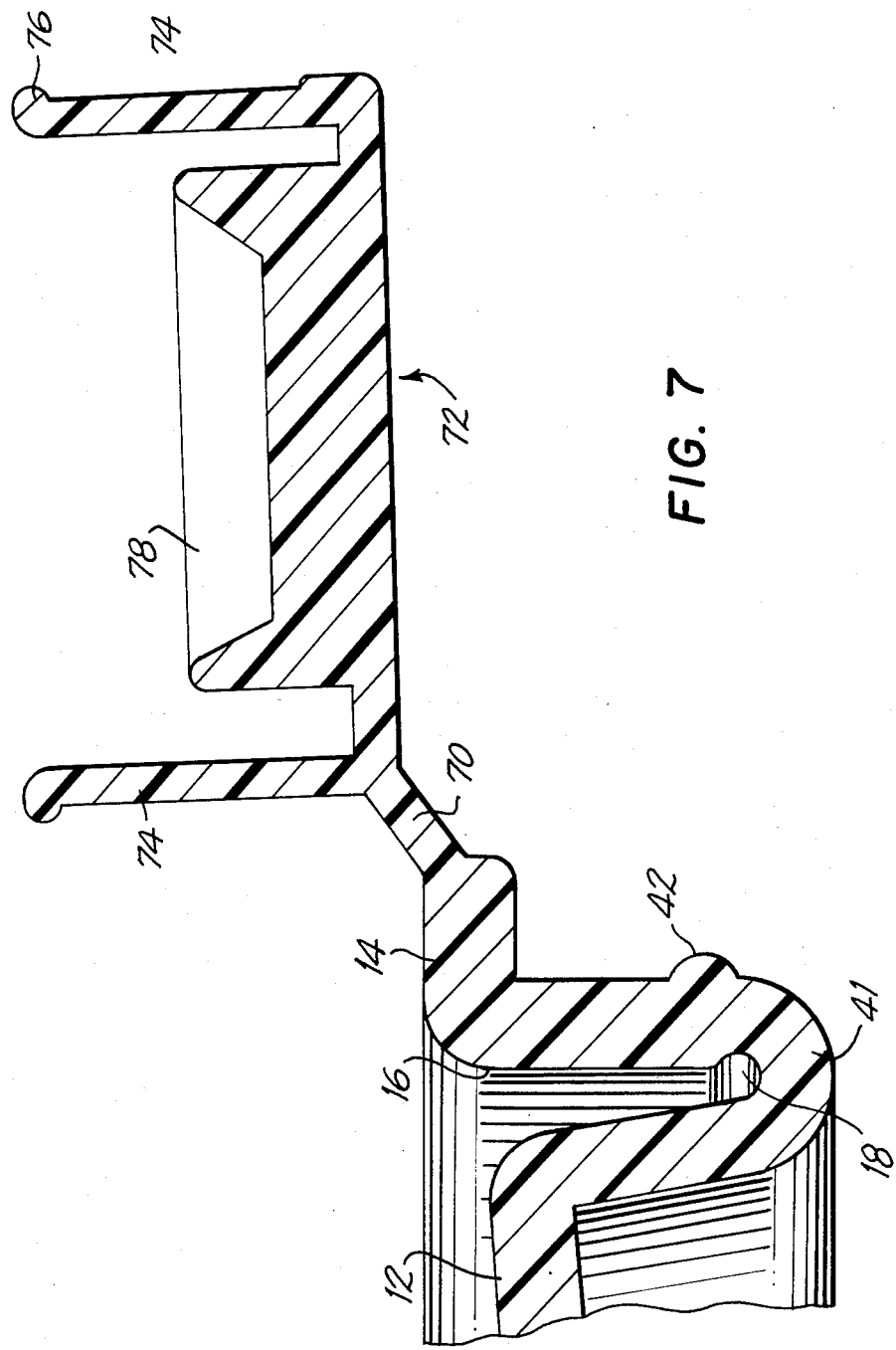
FIG. 7 is an enlarged sectional view similar to FIG. 4, but showing an embodiment of the invention incorporating an integral permanent closure cap of the invention mounted on an integral strap.

Referring to FIG. 7, an embodiment of the invention is shown with a permanent closure 72 integrally mounted on cap 10 at one end of a conventional integral strap 70. Thus, once a container incorporating the cap 10 structure of the invention is filled, closure 72 may be moved in place for permanently closing opening 20. Closure 72 includes a depending central part 78 which extends into and through opening 20. Also, an annular depending locking flange 74 is included with closure 72. The outer end of flange 74 includes locking abutment 76 which, in the closed position of closure 72 wedges into groove 18 for holding closure 72 permanently closed. I will be understood that many forms of permanent closure assemblies may be used to close opening 20 permanently.

Thus, and as will be apparent from the foregoing, there are provided in accordance herewith, methods and apparatus for the release of a contaminated needle hub from the rest of a blood collection assembly and the proper gripping action therefore. Simultaneously, the required resilient properties are provided which enhance the releasing of the wrenched hub of such a contaminated needle so that it will fall easily and safely into the container therefore. Thus, the contaminated needle is removed from any contact with the technician making a contaminated blood collection and from any contact with anyone handling the disposal of goods from a hospital or clinic in the sequence of handling necessary for such removal to a garbage disposal dump or other facility provided for this purpose.

Obviously, it will be apparent that the arrangement of an invention here is of a simple configuration so that the cap of the invention may be vacuum formed or injection molded utilizing assembly line techniques so that many thousands of such caps can be produced on a mass production basis inexpensively.

While the methods and apparatus herein disclosed form preferred embodiments of this invention, this invention is not limited to those specific methods and apparatus, and changes can be made therein without departing from the scope of the invention which is defined in the appended claims.

What is claimed is:

1. A closure device for closing the opening in a contaminated needle collection container and removing contaminated needle hubs from blood collection assemblies, characterized by
  (a) a substantially flat thin closure body;
  (b) attaching means along the edges of said body for the attachment to a contaminated needle collection container;
  (c) an opening positioned substantially centrally of said body;
  (d) said opening being elongated with a first end and a second end;
  (e) said first end being of smaller width than said second end;
  (f) the side walls of said elongated opening diverging from said first end to said second end; and
  (g) a plurality of spaced-apart elongated slots extending from each side wall of said opening, said slots extending perpendicular to the longitudinal axis of said opening.

2. The closure of claim 1, further characterized by
  (a) a circular hole in said body positioned at the end of each of said slots opposite said opening.

3. The closure of claim 1, further characterized by
  (a) said body is round.

4. The closure of claim 1, further characterized by
  (a) said body has a thickness within the range of between about 0.1 millimeters and 2.0 millimeters.

5. The closure of claim 1, further characterized by
  (a) said body is comprised of a material selected from the group consisting of polypropylene, acrylonitrile-butadiene-styrene terpolymer, and metal.

6. The closure of claim 1, further characterized by
  (a) said body is comprised of polypropylene having a thickness of about 1.27 millimeters.

7. The closure of claim 1, further characterized by
  (a) the surface of said body is inclined downwardly from said second end of said opening to said first end thereof.

8. The closure of claim 1, further characterized by a cap for permanently closing said opening comprising
  (a) a cap body;
  (b) an integral strap extending from said closure body to said cap body; and
  (c) cooperating locking means on said closure body and said cap body for permanently closing said opening in said closure body with said cap body.

* * * * *